US008977346B2

(12) United States Patent
Chung-Ming et al.

(10) Patent No.: US 8,977,346 B2
(45) Date of Patent: Mar. 10, 2015

(54) MECHANISM OF QUANTITATIVE DUAL-SPECTRUM IR IMAGING SYSTEM FOR BREAST CANCER

(75) Inventors: Chen Chung-Ming, Taipei (TW); Lee Si-Chen, Taipei (TW); Lee Wan-Jou, Taipei (TW); Chang Che-Wei, Taipei (TW); Lee Ching-Yen, Taipei (TW); Chien Yu-Chun, Taipei (TW); Lee Chia-Yen, Taipei (TW); Yeun-Chung Chang, Taipei (TW); Chiun-Sheng Huang, Taipei (TW)

(73) Assignee: National Taiwan University, Taipei (TW)

( * ) Notice: Subject to any disclaimer, the term of this patent is extended or adjusted under 35 U.S.C. 154(b) by 754 days.

(21) Appl. No.: 13/194,600

(22) Filed: Jul. 29, 2011

(65) Prior Publication Data
US 2013/0030304 A1 Jan. 31, 2013

(51) Int. Cl.
*A61B 6/00* (2006.01)
*A61B 6/04* (2006.01)
*A61B 5/00* (2006.01)
*A61B 5/01* (2006.01)

(52) U.S. Cl.
CPC ............... *A61B 5/0091* (2013.01); *A61B 5/706* (2013.01); *A61B 5/708* (2013.01); *A61B 5/0077* (2013.01); *A61B 5/015* (2013.01)
USPC .......................................... 600/473; 600/474

(58) Field of Classification Search
None
See application file for complete search history.

(56) References Cited

U.S. PATENT DOCUMENTS

| | | | | | |
|---|---|---|---|---|---|
| 4,099,880 | A | * | 7/1978 | Kano | 356/611 |
| 4,991,959 | A | * | 2/1991 | Rueger | 356/251 |
| 6,152,565 | A | * | 11/2000 | Liu et al. | 351/212 |
| 6,765,663 | B2 | * | 7/2004 | Byren et al. | 356/152.1 |
| 7,620,265 | B1 | * | 11/2009 | Wolff et al. | 382/276 |
| 2003/0164459 | A1 | * | 9/2003 | Schardt et al. | 250/492.3 |
| 2004/0181375 | A1 | * | 9/2004 | Szu et al. | 703/2 |
| 2005/0195410 | A1 | * | 9/2005 | Chien et al. | 356/622 |
| 2009/0118600 | A1 | * | 5/2009 | Ortiz et al. | 600/306 |
| 2009/0148036 | A1 | * | 6/2009 | Aoyama | 382/154 |
| 2009/0318815 | A1 | * | 12/2009 | Barnes et al. | 600/473 |
| 2012/0098972 | A1 | * | 4/2012 | Hansen et al. | 348/164 |

OTHER PUBLICATIONS

Wirth et al.: "Nonrigid Mammogram Registration Using Mutual Information", SPIE Medical Imaging: Image Processing, San Diego USA, Feb. 2002, vol. 4684, pp. 562-573.

* cited by examiner

*Primary Examiner* — Long V Le
*Assistant Examiner* — Bradley Impink

(57) ABSTRACT

A mechanism of quantitative dual-spectrum IR imaging (QDS-IR) system for examining the breast cancer is reported. The major mechanism of the system is a pair of long-wave Infra-red (LIR) and middle-wave Infra-red (MIR) cameras with the keen temperature sensitivity and the high spatial resolution. The optical axes of cameras are calibrated by the help of two calibration makers set up on the seat for carrying an object to make them parallel to each other and locate on the same level. The design provides an imaging system with the high reproducibility supported by 7 free degrees and the high adjustability. The proposed system could ensure the positions of the object and two cameras are the same at the different time points and find the best relative positions between the seat and two cameras for the objects with different body types. Therefore, it has potential ability to detect breast cancer or monitor the effect of chemotherapy.

12 Claims, 6 Drawing Sheets

MECHANISM OF QUANTITATIVE DUAL-SPECTRUM IR IMAGING SYSTEM FOR BREAST CANCER

FIELD OF THE INVENTION

The invention relates to a mechanism of quantitative dual-spectrum IR imaging system for breast cancer. More specifically, this invention relates to an image system with MIR (middle-wave Infra-red) and LIR (long-wave Infra-red) cameras for accepting longitudinal infrared images over several time points in order to obtain more usable information of detecting the breast cancer.

BACKGROUND OF THE INVENTION

Breast cancer has been ranked the leading cause of cancer deaths for females. Common imaging modalities, such as X-ray mammograms, MRI images and Ultrasound, used to detect breast cancers at present are mammogram and breast sonography. However, they both do not have a sufficient spatial resolution and are not sensitive enough to detect breast cancers. Although the MRI and the PET have the potential for early detection of breast cancers, they are both very costly and not usually used as the first-line defense.

Due to the advantages of non-invasion, non-contact, passivity, non-radiation and the ability of detecting the slight variations of temperature caused by neovascularization, Infrared imaging technique has been developed and employed for assessing chemotherapy treatment response. Serving as a medical imaging modality, the Infra-red (IR) image reveals the heat distribution on the surface of the human body. Cancerous tissues tend to have a higher temperature signature than their surrounding normal tissues, and for this reason, IR image has long been studied in hope to serve as an indicator for cancerous breast tissues. Nevertheless, the usefulness of IR images in detecting breast cancers at a single time is not usually enough to assess the chemotherapy treatment response and early detection due to the physiological and environmental influence on the skin temperature distribution. Alternatively, the IR images in detecting tumors over several time points attempt to determine the malignancy of breast tissues based on the variation of heat pattern.

Therefore, this present invention proposes to develop a mechanism used in passive medical imaging modality, called mechanism of quantitative dual-spectrum IR imaging for detection of malignant tumors in breast.

The accuracy of assessing the chemotherapy treatment response would be effected from the mechanism of imaging system. In the prior art, for example, X-ray mammograms, MRI images, Ultrasound and IR images (refer to Wirth, M. A., Narhan, J., Gray, D., "Nonrigid mammogram registration using mutual information," Proc. SPIE. 2002), the mechanisms of the traditional imaging system for examining the breast cancer lack of the properties of the high reproducibility and the high adjustability, such as all adjustments are performed manually so that the reproducibility is low for examination at every different time points, the pair of cameras have to be can be calibrated after removing and installing them back and there are no armrests on the seat for carrying the object to retain a posture of the object in each photoing. Based on the above-mentioned, there are inhomogeneous and anisotropic soft tissues over the breast so the heat patterns will transform for the posture and the position of the patient changed at different time points. It will add the difference of the analysis process.

Therefore, the inventor thought of the idea of an improvement invention after considering the shortage of the prior art and finally invented the case of "mechanism of quantitative dual-spectrum IR imaging system for breast cancer". The system is provided to obtain more usable information as testing at single time point and at several time points. Then, the obtained longitudinal dual spectrum infrared images can quantify the effect of chemotherapy by adding the information of heat changing with time via an image registration method, Dual-Spectrum Heat Pattern Separation (DS-HPS) algorithm (U.S. application Ser. No. 12/965,642, Dec. 10, 2010, filed by the applicant). The effects of chemotherapy on breast cancer are effectively traced and evaluated by using this method. The invention is briefly described as follows.

SUMMARY OF THE INVENTION

In the present application, the goal of "the mechanism of quantitative dual-spectrum IR (QDS-IR) imaging system" is provided with an imaging system with the high reproducibility and the high adjustability. Besides, the demand of the high reproducibility is to ensure the positions of the object and two cameras are the same for the DS-IR spectrogram of the breast shoot at the different time points. And the demand of the high adjustability is used to find the best relative positions between the seat and two cameras for the objects with different body types.

Such an mechanism of QDS-IR system can obtain the longitudinal infrared images at single time point and at several time points, and make the invented system extremely suitable for examining the human body applications including non-invasive detection of human body, assessing chemotherapy treatment response, early detection and etc.

According to the first aspect of the present invention, an mechanism of quantitative dual-spectrum IR imaging system is provided. The image system for obtaining a Dual-Spectrum spectrogram, includes: a platform; a first camera having a first optical axis disposed on the platform; a second camera having a second optical axis disposed on the platform; a mechanism having a track; a seat carrying an object and connected with the platform via the mechanism, wherein the object has a posture, and the seat has two armrests to retain the posture of the object in each photoing, and the seat is configured to move along the track for examining the objects of different body figures; a first calibration marker disposed on the seat to calibrate the first optical axis; and a second calibration marker disposed on the seat to calibrate the second optical axis, wherein the first optical axis and the second optical axis are parallel to each other and located on the same level.

According to the second aspect of the present invention, a method for obtaining a Dual-Spectrum spectrogram, comprising the following steps of: configuring a first camera having a first optical axis and a second camera having a second optical axis on a platform; configuring a seat carrying an object having a specific figure and connected with the platform via a track, wherein the seat has two armrests; moving the seat along the track for examining the specific figure of the object; calibrating the first optical axis and the second optical axis so that the first optical axis and the second optical axis are parallel to each other and located on the same level; and retaining a posture of the object in each photoing through the assistance of the two armrests.

According to the third aspect of the present invention, an image system, comprising: a immobilizing apparatus retaining a posture of an object in each photoing; a first camera having a first optical axis; a second camera having a second optical axis; a first calibration marker calibrating the first optical axis; and a second calibration marker calibrating the second optical axis so that the first optical axis and the second optical axis are parallel to each other and located on the same level.

The above aspects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only it is not intended to be exhaustive or to be limited to the precise form disclosed.

Figure 1:
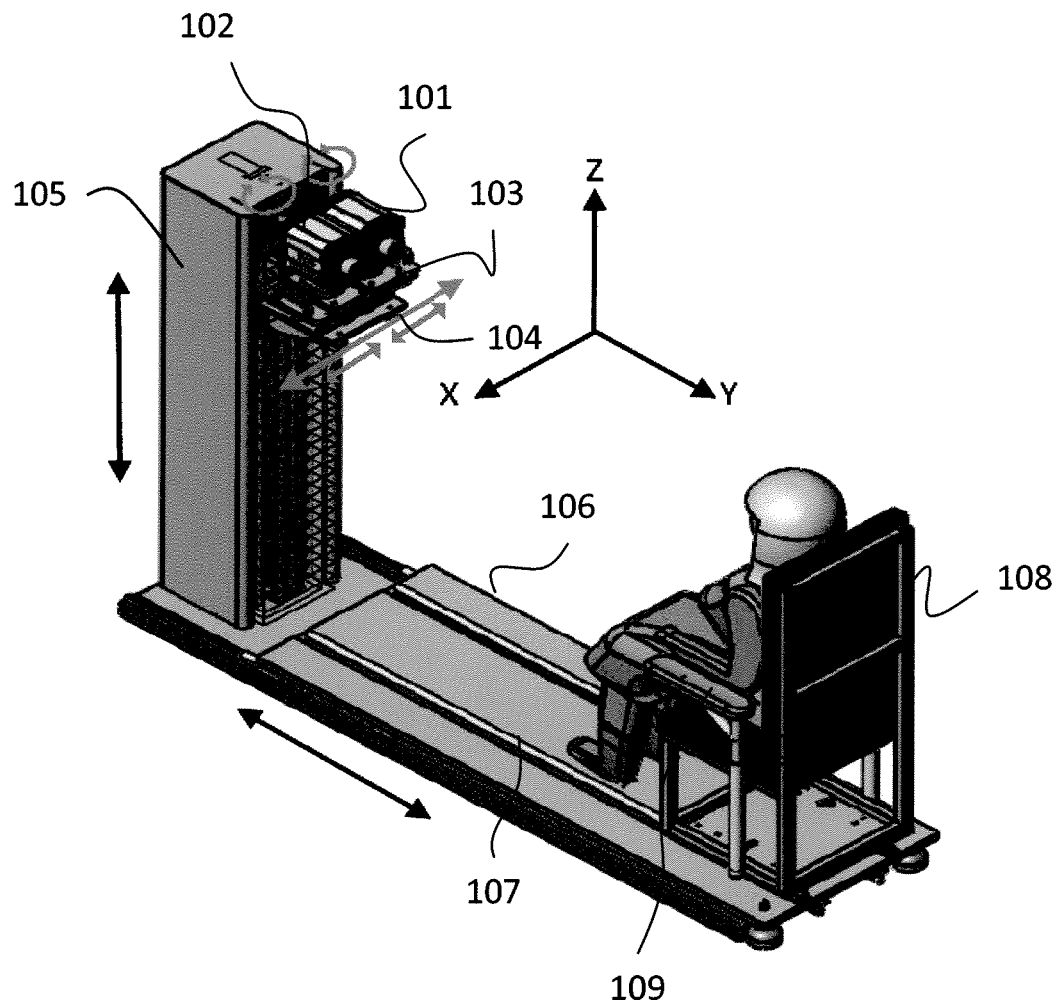
FIG. 1 shows that the diagram of the present invention for obtaining a Dual-Spectrum spectrogram.

Please refer to FIG. 1, which shows that the diagram of the present invention for obtaining a Dual-Spectrum spectrogram. A slab 103 is used to support both the LIR camera 101 and the MIR camera 102, which are disposed on the platform 104, the platform 104 is installed on a base 105, the base 105 is connected with a seat for carrying an object 108 through a mechanism 106, there is a track 107 on the mechanism 106 for moving the seat 108, a pair of armrests 109 (the other one is not shown in the figure) is installed on the seat 108, and a calibrating board with two cross line centers is installed on the upper of the seat 108 (the board is not shown in the figure). Preferably, the major mechanism of the DS-IR imaging system 100 is a pair of LIR camera 101 (the wavelength range: 8-9.2 μm) and MIR camera 102 (the wavelength range: 3-5 μm) with the keen temperature sensitivity and the high spatial resolution. Preferably, the adapted IR cameras (provided by FUR Systems) have 320×256 detectors of the pixel points, and their temperature sensitivity and spatial resolution are 0.02° C. and about 0.6 mm at 1 m distance away, respectively.

Figure 2:
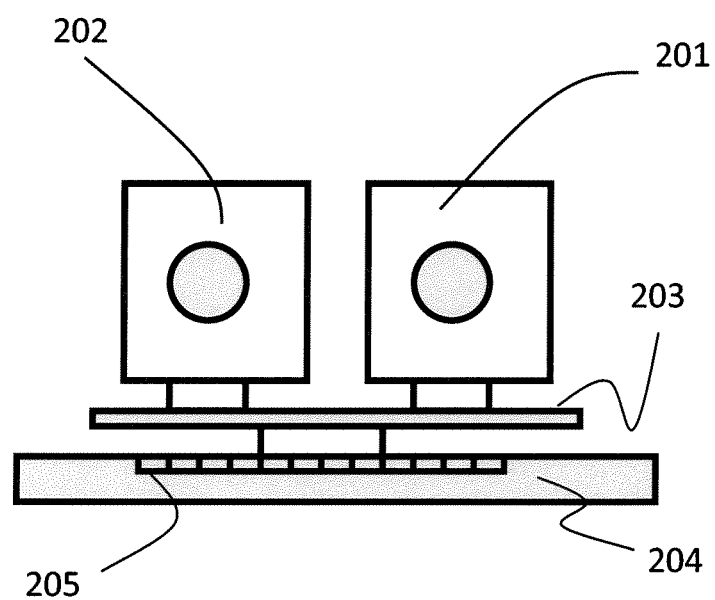
FIG. 2 shows that a pair of cameras disposed on the platform.

Please refer to FIG. 2, which shows that a pair of cameras (201, 202) corresponding to (101, 102) in FIG. 1 are supported on the slab 203 disposed on the platform 204 corresponding to (103, 104) in FIG. 1. The pair of cameras (201, 202) is installed on the mechanism 106 through the base 105 and the seat for carrying an object 108 is also installed on the same mechanism 106 in order to ensure they are in the same level system. Preferably, the pair of cameras (201, 202) can be removed from the platform 204 when the slab 203 is removed from the platform 204, and the platform 204 will not be moved. Preferably, after calibrating the pair of cameras (201, 202), the pair of cameras (201, 202) has a specific position related to the seat 108, the information of the specific position can be obtained from the scale 205 on the platform 204 and recorded. Therefore, the position of the pair of cameras (201, 202) will be the same at every different time points for the examination.

Figure 3A:
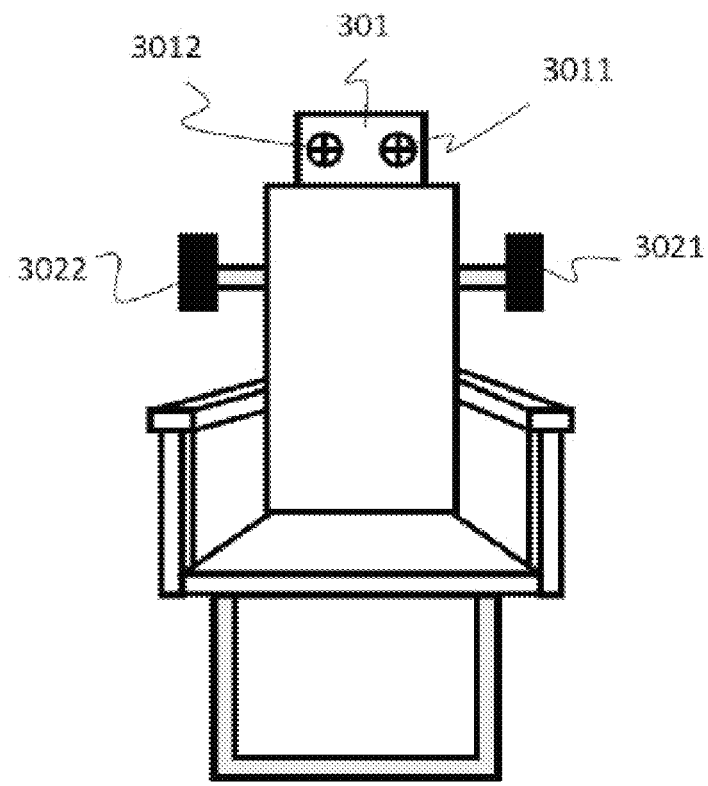
FIG. 3(a) shows that a calibrating board with two cross line centers is disposed on the upper of the seat for carrying an object.
Figure 3B:
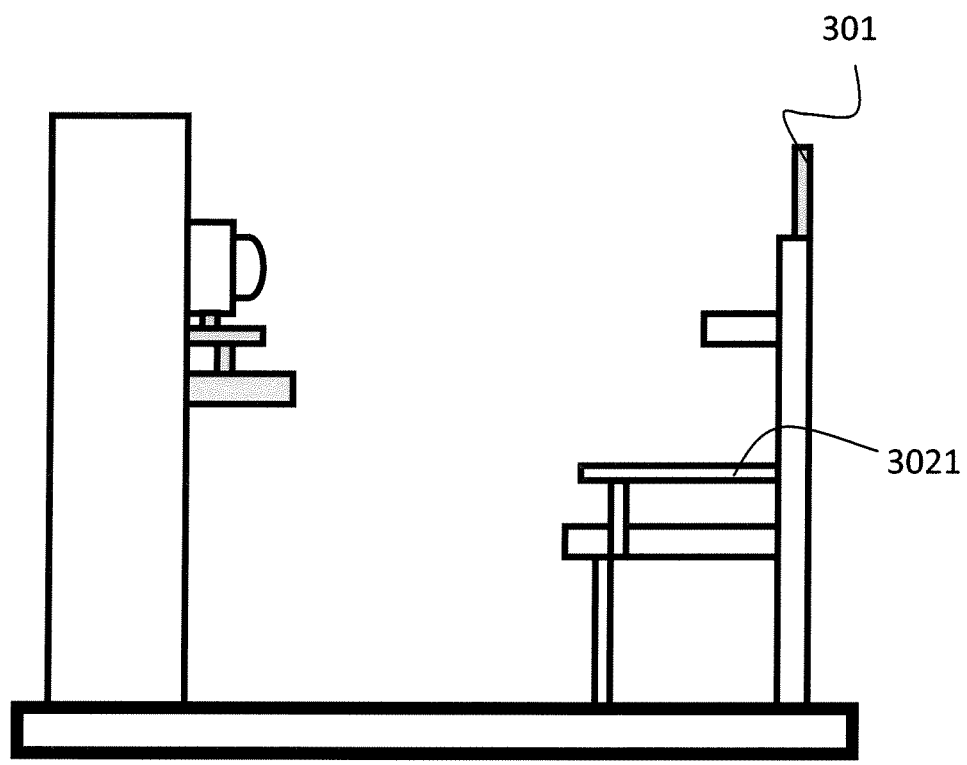
FIG. 3(b) shows that the designed armrests of the seat for ensuring that the body posture and the lift height of the arms remain the same on each examination.

Besides, we also designed a calibrating apparatus to ensure these two optical axes of LIR and MIR cameras are in the same plane. Please refer to FIG. 3(a), the calibrating apparatus having a calibrating board 301 with two cross line centers (3011, 3012) is installed on the upper of the seat for carrying an object 108. Preferably, we designed the armrests (3021, 3022) on the left and right sides of the seat 108 to make sure that the body posture and the lift height of the arms remain the same on each examination, and the object also feels with ease, as shown in FIG. 3(b).

As shown in FIG. 1, the system 100 has seven free degrees including: (1) each camera (101 or 102) can move freely along X direction and rotate freely on the X-Y plane, so that four free degrees exist, (2) the platform 104 supporting two cameras (101, 102) can move along X and Z directions, so that two free degrees exist, (3) the seat for carrying an object 108 is disposed on a mechanism 106, and can move along the track 107 on the mechanism 106 in Y direction, so that one free degree exists. Therefore, there are seven free degrees in the system 100, which is convenient to calibrate two optical axes of these two QDS-IR cameras (101, 102) being parallel to each other.

Preferably, the imaging system 100 has the high mobility, the facilitated operation and the following characteristics: (1) the laser is used to calibrate the optical axes of the cameras (101, 102) in order to ensure they are parallel to the seat for carrying an object 108, (2) the platform 104 which loads two cameras (101, 102) can load 50 KG, and after the calibrating process, two cameras (101, 102) also can be removed to perform other examinations without calibrating them again. Because a slab 103 for supporting the pair of cameras (101, 102) is disposed on the platform 104, so the pair of cameras (101, 102) can be removed from the platform 104 when the slab 103 is removed from the platform 104, and the platform 104 will not be moved. Preferably, after calibrating the pair of cameras (101, 102), the platform 104 has a specific distance and angle to the seat 108, when the pair of cameras (101, 102) is removed, the specific distance and angle of the platform 104 to the seat 108 remain the same, so that the calibrating process is not necessary when the pair of cameras (101, 102) is installed back to the platform 104. Besides, these two removed cameras (101, 102) can be used to photo IR images of different parts of the body, and also may be suited for animal experiments due to the facilitation of carrying off the animal center, (3) the motor automatically controls the platform up and down along Z axis without the operation of the operators, (4) the moveable distance of the seat 108 is 150 cm along Z axis so that the detectable range of the system 100 is widened. For example, the QDS-IR system 100 is used to forecast the possibility of obtaining the cerebral apoplexy by the narrow estimation of the carotid artery, or do research of the leg varicosity, (5) the distance between the seat 108 and the pair of cameras (101, 102) can be adjusted along Y axis according to the environment space. Because the above-mentioned characteristics, such as the seat 108 is moveable front and back and the platform 104 carrying the pair of cameras (101, 102) is moveable up and down, the front of the body can be photoed and more useful information of the temperature in every region of the body can be obtained.

Figure 4A:
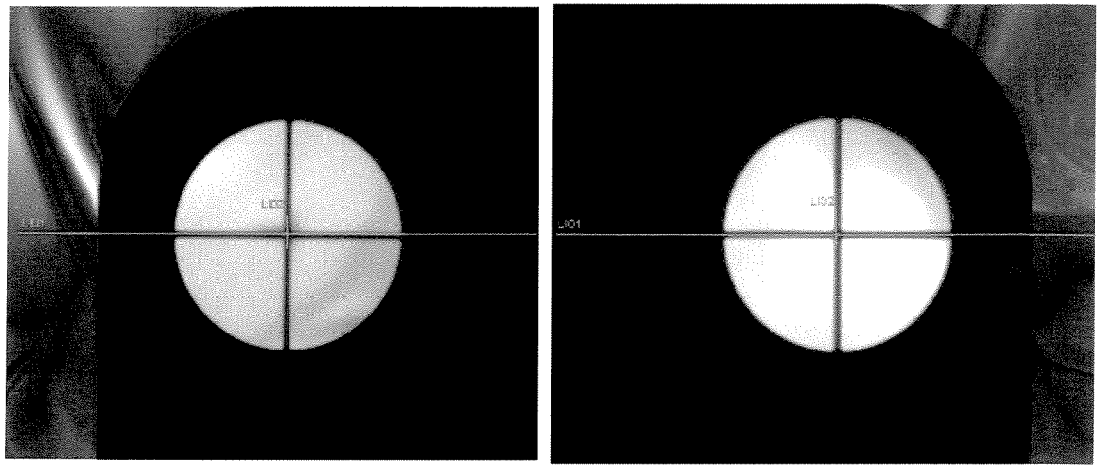
FIG. 4(a) shows that the result of calibrating LW and MIR cameras for ensuring these two optical axes of LIR and MIR cameras are in the same plane at the long distance.
Figure 4B:
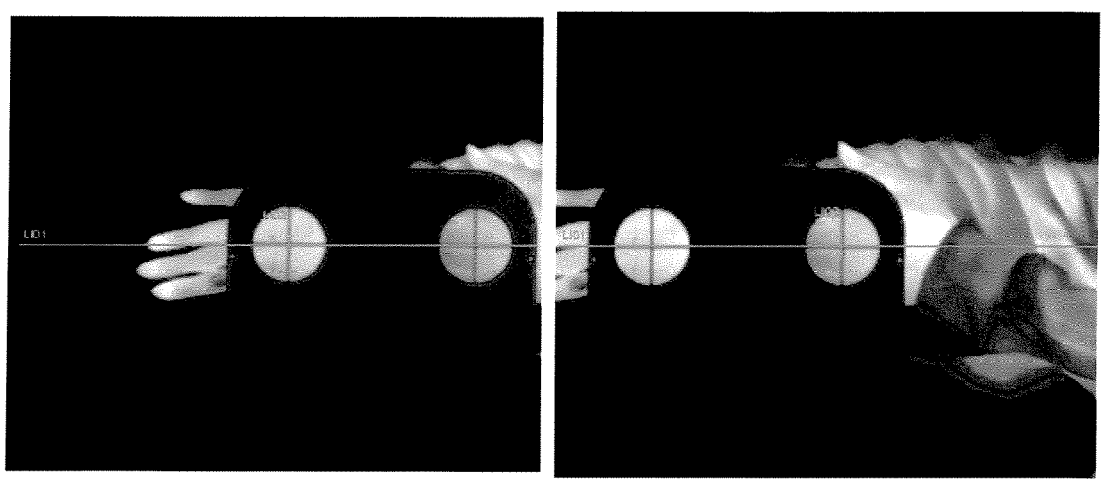
FIG. 4(b) shows that the result of calibrating LIR and MIR cameras for ensuring these two optical axes of LIR and MIR cameras are in the same plane at the short distance.

Please refer to FIG. 4(a) and FIG. 4(b), which show that the result of calibrating LIR and MIR cameras for ensuring these two optical axes of LIR and MIR cameras are in the same plane at the long distance and the short distance, respectively. The following descriptions are used to calibrate two optical axes of these two QDS-IR cameras: (1) two cross centers of the first and the second calibration markers disposed on the seat are used to be the centers of the first and the second optical axis respectively, (2) we calibrate one of these two cameras: moving the seat for carrying an object toward the camera and adjusting every free degree of the camera, so that the center of the first or second optical axis can aim at the corresponding cross center, (3) we move the seat for carrying an object away from the camera and fine tune every free degree of the camera, so that the center of its optical axis can aim at the cross center, (4) repeating the steps (2) and (3) until the center of its optical axis aims at the cross center, so we can make sure that its optical axis is parallel to the plane of the platform, (5) finally, the free degree of the calibrated camera is fixed and then, repeating the steps (2) to (4) for the other camera.

Figure 5A:
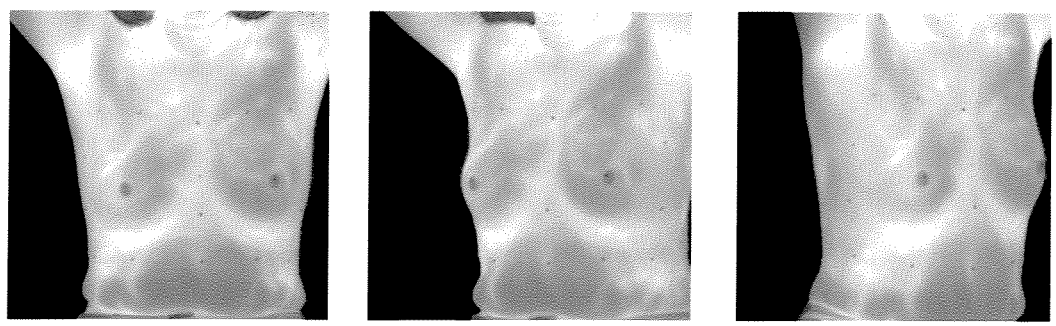
FIGS. 5(a) and (b) show that a set of the front and lateral images of LIR and MIR obtained by the QDS-IR system, respectively.
Figure 5B:
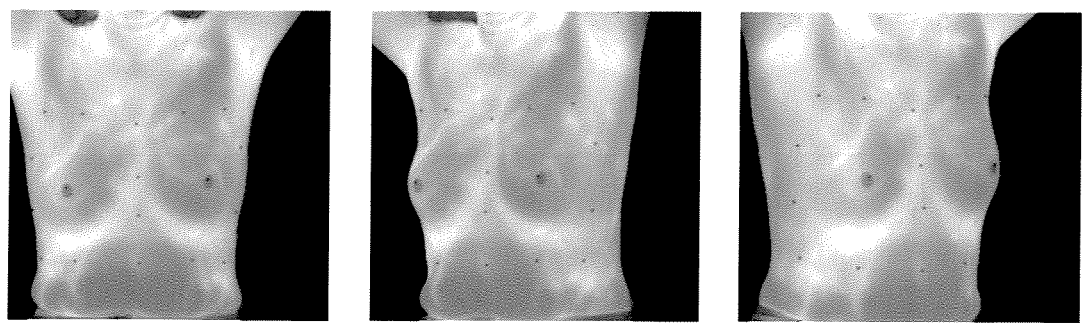

After calibrating the QDS-IR system, the photographing flow for obtaining a Dual-Spectrum spectrogram is performed at the temperature 25° C. as follows: (1) after entering the laboratory, the object sits still about 10 to 15 minutes to prevent from external factors, such as sweating and so on, which influence the infrared information, (2) a plurality of makers is pasted on the object's body for the orientation, (3) photographing a plurality of the front and lateral images of LIR and MIR at the distance 2.5 and 3.5 m away, respectively. Please refer to FIGS. 5(a) and (b), which show that a set of the front and lateral images of LIR and MIR by the QDS-IR system, respectively.

There are still other embodiments, which are described as follows.

Embodiment Could be:

1. An image system for obtaining a Dual-Spectrum spectrogram, comprising: a platform; a first camera having a first optical axis disposed on the platform; a second camera having a second optical axis disposed on the platform; a mechanism having a track; a seat carrying an object and connected with the platform via the mechanism, wherein the object has a posture, and the seat has two armrests to retain the posture of the object in each photoing, and the seat is configured to move along the track for examining the objects of different body figures; a first calibration marker disposed on the seat to calibrate the first optical axis; and a second calibration marker disposed on the seat to calibrate the second optical axis, wherein the first optical axis and the second optical axis are parallel to each other and located on the same level.

2. The system as described in Embodiment 1, wherein the first camera and the second camera are a long-wave Infra-red (LIR) camera and a middle-wave Infra-red (MIR) camera respectively.

3. The system as described in Embodiment 1, wherein the platform has a first plane, the first camera and the second camera are configured on the first plane to move along a first direction and to be rotated on the first plane, and the platform is configured to move along one of a second direction and a third direction.

4. The system as described in Embodiment 3, wherein the first direction is a horizontal direction, and the first plane is a horizontal plane.

5. The system as described in Embodiment 3, wherein the track has a forth direction which is perpendicular to the first direction.

6. The system as described in Embodiment 3, wherein the first direction and the forth direction are parallel to the first plane.

7. The system as described in Embodiment 3, wherein the second direction is perpendicular to the third direction.

8. The system as described in Embodiment 3, wherein the third direction is vertical to the first plane.

9. The system as described in Embodiment 1, wherein the first calibration marker and the second calibration marker are cross line centers.

10. The system as described in Embodiment 1 further comprises a slab supporting the first camera and the second camera, wherein the slab is disposed on the platform, and after calibrating the first camera and the second camera, the first camera and the second camera can be removed from the platform when the slab is removed from the platform, so that the first camera and the second camera can be installed back to the platform without calibrating thereon.

11. The system as described in Embodiment 1, wherein the system is used for obtaining one of a single time spectrogram and a time-series spectrogram.

12. A method for obtaining a Dual-Spectrum spectrogram, comprising the steps of: configuring a first camera having a first optical axis and a second camera having a second optical axis on a platform; configuring a seat carrying an object having a specific figure and connected with the platform via a track, wherein the seat has two armrests; moving the seat along the track for examining the specific figure of the object; calibrating the first optical axis and the second optical axis so that the first optical axis and the second optical axis are parallel to each other and located on the same level; and retaining a posture of the object in each photoing through the assistance of the two armrests.

13. The method as described in Embodiment 12 further comprising a step of disposing a first calibration marker and a second calibration marker on the seat for respectively calibrating the first optical axis and the second optical axis.

14. The method as described in Embodiment 13, wherein the first calibration marker and the second calibration marker are cross line centers.

15. The method as described in Embodiment 12, wherein the method is used for obtaining one of a single time spectrogram and a time-series spectrogram.

16. An image system, comprising: a immobilizing apparatus retaining a posture of an object in each photoing; a first camera having a first optical axis; a second camera having a second optical axis; a first calibration marker calibrating the first optical axis; and a second calibration marker calibrating the second optical axis so that the first optical axis and the second optical axis are parallel to each other and located on the same level.

17. The system as described in Embodiment 16, wherein the first camera and the second camera are a long-wave Infra-red (LIR) camera and a middle-wave Infra-red (MIR) camera respectively.

18. The system as described in Embodiment 16, wherein the immobilizing apparatus is a seat for carrying an object having a pair of armrests.

19. The system as described in Embodiment 16, wherein the first calibration marker and the second calibration marker are cross line centers.

20. The system as described in Embodiment 16, wherein the system is used for obtaining one of a single time spectrogram and a time-series spectrogram.

In conclusion, the imaging system for obtaining a Dual-Spectrum spectrogram is proposed in the present invention. For assessing chemotherapy treatment response and early detection via the DS-Spectrogram system, MIR and LIR cameras are used to obtain the emitted MIR and LIR waves from regions of the body skin, such as the head, the eyes, the face, the neck, the breasts, the arms, the legs, the belly and so on, and the information of the temperature in the same region can be obtained after registering the MIR and LIR images at the single time point. Then, the effective quantities of the high temperature and basal body temperature tissues in one pixel can be estimated by the Blind Source Separation (BSS). In order to decrease the effect from the shooting angle, the optical axes of two cameras are calibrated to be parallel each in the DS-IR system architecture. However, there is still a horizontal displacement so that a non-linear and non-uniform deformation appeared between the MIR image and the LIR image. Therefore, in each shoot, we use the points marked on the experimental subject serve as the control points of the TPS model in the IR image, and establish manually the interrelationship of the control points on two IR images to register the two IR images. These suggest the proposed algorithm could prove that the DS-IR system adding time information has potential ability to detect breast cancer or monitor the effect of chemotherapy. Besides, the system is used not only for obtaining one of a single time spectrogram, but also a time-series spectrogram.

Based on the above descriptions, it is understood that the present invention is indeed an industrially applicable, novel and obvious one with values in industrial development. While the invention has been described in terms of what are presently considered to be the most practical and preferred embodiment, it is to be understood that the invention should not be limited to the disclosed embodiment. On the contrary, it is intended to cover numerous modifications and variations included within the spirit and scope of the appended claims which are to be accorded with the broadest interpretation so as to encompass all such modifications and variations. Therefore, the above description and illustration should not be taken as limiting the scope of the present invention which is defined by the appended claims.

What is claimed is:

1. An image system for obtaining a Dual-Spectrum spectrogram, comprising:
    a platform;
    a first camera having a first optical axis disposed on the platform;
    a second camera having a second optical axis disposed on the platform;
    a mechanism having a track;
    a seat connected with the platform via the mechanism, wherein the seat has two armrests to retain a posture of an object, and the seat is configured to move along the track;
    a first calibration marker disposed on the seat to calibrate the first optical axis; and
    a second calibration marker disposed on the seat to calibrate the second optical axis, wherein the platform has a first plane, the first camera and the second camera are configured on the first plane to move along a first direction and to be rotated on the first plane, the platform is configured to move along one of a second direction and a third direction, the track has a fourth direction which is perpendicular to the first direction, the first direction and the fourth direction are parallel to the first plane, and the first calibration marker and the second calibration marker are cross line centers, to adjust the first optical axis and the second optical axis to be parallel to each other and located on the same level.

2. The system as claimed in claim 1, wherein the first camera and the second camera are a long-wave Infra-red (LIR) camera and a middle-wave Infra-red (MIR) camera respectively.

3. The system as claimed in claim 1, wherein the first direction is a horizontal direction, and the first plane is a horizontal plane.

4. The system as claimed in claim 1, wherein the second direction is perpendicular to the third direction.

5. The system as claimed in claim 1, wherein the third direction is vertical to the first plane.

6. The system as claimed in claim 1 further comprises a slab supporting the first camera and the second camera, wherein the slab is disposed on the platform, and after calibrating the first camera and the second camera, the first camera and the second camera can be removed from the platform when the slab is removed from the platform, so that the first camera and the second camera can be installed back to the platform without calibrating thereon.

7. The system as claimed in claim 1, wherein the system is used for obtaining one of a single time spectrogram and a time-series spectrogram.

8. An image system, comprising:
    a platform;
    an immobilizing apparatus used for retaining an object at a specific posture;
    a first camera having a first optical axis disposed on the platform;
    a second camera having a second optical axis disposed on the platform;
    a first calibration marker configured to facilitate calibration of the first optical axis; and
    a second calibration marker configured to facilitate calibration of the second optical axis,
    wherein the platform, the first camera, the second camera, and the immobilizing apparatus have a total of seven degrees of freedom of adjustability, the first calibration marker has a first exact center, the second calibration marker has a second exact center, and the first calibration marker and the second calibration marker respectively indicate the first exact center and the second exact center so that the first optical axis and the second optical axis are adjusted to be parallel to each other and located on the same level.

9. The system as claimed in claim 8, wherein the first camera and the second camera are a long-wave Infra-red (LIR) camera and a middle-wave Infra-red (MIR) camera respectively.

10. The system as claimed in claim 8, wherein the immobilizing apparatus is a seat for carrying an object, and the seat has a pair of armrests.

11. The system as claimed in claim 8, wherein the first calibration marker and the second calibration marker are cross line centers.

12. The system as claimed in claim 8, wherein the system is used for obtaining one of a single time spectrogram and a time-series spectrogram.

* * * * *